(12) United States Patent
Niessner et al.

(10) Patent No.: US 6,231,876 B1
(45) Date of Patent: May 15, 2001

(54) USE OF WATER-SOLUBLE COPOLYMERS AS ACTIVE INGREDIENTS IN COSMETICS

(75) Inventors: Manfred Niessner, Schifferstadt; Claudia Nilz, Rödersheim-Gronau; Peter Hössel, Schifferstadt; Stephan Kothrade, Limburgerhof; Axel Sanner, Frankenthal, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/269,337

(22) PCT Filed: Sep. 29, 1997

(86) PCT No.: PCT/EP97/05354

§ 371 Date: Mar. 25, 1999

§ 102(e) Date: Mar. 25, 1999

(87) PCT Pub. No.: WO98/14164

PCT Pub. Date: Apr. 9, 1998

(30) Foreign Application Priority Data

Sep. 30, 1996 (DE) ................................. 196 40 363

(51) Int. Cl.[7] ............................ A61K 7/075; A61K 7/50; A61K 7/06; A61K 7/11; A61K 7/09

(52) U.S. Cl. ...................... 424/401; 424/401; 424/70.1; 424/70.2; 424/70.11; 424/70.17; 510/119; 510/130; 514/944; 514/945

(58) Field of Search .................... 424/401, 70.1, 424/70.2, 70.11, 70.122, 70.19; 514/937, 944; 510/119, 130

(56) References Cited

U.S. PATENT DOCUMENTS

| | | | |
|---|---|---|---|
| 4,722,958 | 2/1988 | Sauer et al. | 524/379 |
| 5,128,508 | 7/1992 | Klingel | 219/127 |
| 5,270,379 | 12/1993 | McAndrew et al. | 524/555 |
| 5,373,076 | 12/1994 | Pinschmide et al. | 526/303 |
| 5,578,678 | * 11/1996 | Hartman et al. | 525/54.3 |

FOREIGN PATENT DOCUMENTS

| | | |
|---|---|---|
| 510246 | 10/1992 | (EP) . |
| 1007341 | 10/1965 | (GB) . |
| 1044956 | 10/1966 | (GB) . |
| 1082016 | 9/1967 | (GB) . |
| 06122725 | 11/1990 | (JP) . |
| 3223304 | 11/1990 | (JP) . |
| 96/03969 | 2/1996 | (WO) . |

OTHER PUBLICATIONS

U.S. application No. 09/230,352, Neissner et al., filed Jun. 25, 1999.

Lochhead et al., *Cosmetics and Toiletries*, 103, Dec. 1988, p. 23–61.

Fikentscher, *Cellulose Chemie*, 13, 1932, pp. 58–64, 71 and 74 (English abstract provided).

* cited by examiner

Primary Examiner—Diana Dudash
Assistant Examiner—Gina Yu
(74) *Attorney, Agent, or Firm*—Keil & Weinkauf

(57) ABSTRACT

A cosmetic composition comprising water-soluble copolymer, which as characteristic structural elements comprises a) vinylcarboxamide units of the general formula I

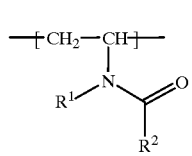

(I)

where $R^1$ and $R^2$ independently of one another are H, alkyl, cycloalkyl, aryl or aralkyl, and b) units of the general formula II

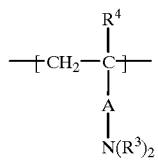

(II)

where

A is a chemical bond or an alkylene group, the radicals $R^3$ independently of one another are H, alkyl, cycloalkyl, aryl or aralkyl, or together with the nitrogen atom to which they are bonded, form an unsubstituted, mono- or polysubstituted, five- to seven-membered, heterocyclic, aromatic or nonaromatic ring, which if appropriate contains one or two further heteroatoms, selected from among O, N and S, it being possible for the heterocyclic ring to be fused to a further five- or six-membered, aromatic or nonaromatic ring, $R^4$ is H, alkyl or aralkyl.

11 Claims, No Drawings

USE OF WATER-SOLUBLE COPOLYMERS AS ACTIVE INGREDIENTS IN COSMETICS

The invention relates to the use of water-soluble copolymers as constituents of cosmetic compositions, and to cosmetic compositions which contain these copolymers.

Polymers are frequently used in cosmetics and medicine. In soaps, creams and lotions, for example, they are generally used as a formulation aid, e.g. as a thickener, foam stabilizer or water absorbent, or alternatively for alleviating the irritant action of other ingredients or for improving the dermal administration of active ingredients. Their object in hair cosmetics, however, is to influence the properties of the hair. Thus conditioners are employed in order to improve the dry and wet combability, feel, luster and appearance, and to impart antistatic properties to the hair. They can furthermore have a strengthening action by forming hydrophobic films on the hair.

Preferably, water-soluble polymers having polar, often cationic, functionalities are employed which have a greater affinity for the structurally related negative surface of the hair. The structure and mode of action of various hair treatment polymers are described in Cosmetics & Toiletries 103 (1988) 23. Commercially available conditioner polymers are, for example, cationic hydroxyethylcellulose, cationic polymers based on N-vinylpyrrolidone, acrylamide and diallyldimethylammonium chloride or silicones.

U.S. Pat. No. 4,713,236 describes hair conditioners based on polymers containing vinylamine units. Mention may be made here, in particular, of polyvinylamine and its salts, α-substituted polyvinylamines such as, for example, poly-(α-aminoacrylic acid) or alternatively copolymers which, beside vinylamine, contain comonomers such as vinyl alcohol, acrylic acid, acrylamide, maleic anhydride, vinylsulfonate and 2-acrylamido-2-methyl-propanesulfonic acid in copolymerized form. The possible applicability of copolymers having recurring vinylamine and vinylcarboxamide units as effective constituents of a hair conditioner is not investigated in this document.

WO-A-96/03969 describes hair care compositions, comprising an N-vinylformamide homopolymer or a copolymer of N-vinylformamide units and a further vinyl monomer, selected from among styrenes, alkyl esters of acrylic and methacrylic acid, vinyl esters of the formula $CH_2=CH-OCO$-alkyl, N-alkyl-substituted acrylamides and methacrylamides, esters of fumaric, itaconic and maleic acid, vinyl ethers, hydroxy-functionalized acrylates and methacrylates, acrylamide, non-alkyl-substituted acrylamides and cyclic amides. vinylpyrrolidone is mentioned as an actual example of a cyclic amide. Further examples of vinyl monomers are secondary, tertiary and quaternary amines, such as dimethyldiallylammonium chloride, t-butylaminoethyl methacrylate, dimethylaminoethyl methacrylate, diethylaminoethyl methacrylate, dimethylaminopropyl methacrylate and the quaternized derivatives thereof.

JP 06 122 725 describes pulverulent N-vinylformamide homo- and copolymers. These polymers are used, for example, as a constituent of toners, chromatography materials, carriers for immunodiagnostics and fillers for dyes and cosmetics. Suitability of these polymers as conditioning agents, in particular as conditioning agents for shampoos, is not described.

Hydrolyzed oligomers of N-vinylformamide are disclosed in U.S. Pat. No. 5,373,076. Hypothetical areas of application mentioned for these polymers are, inter alia, adhesives, binders, water treatment, paper manufacture, petroleum and minerals extraction, medicine and personal hygiene.

EP 510 246 and the Japanese specification JP 3223 304 disclose crosslinked, mainly anionic homo- and copolymers of N-vinylcarboxamides, which are employed as water absorbers and thickeners, for example in the cosmetic field.

Copolymers of acrylamide and (meth)acrylic acid, which as further monomers can also contain N-vinylcarboxamides, are likewise used according to DE 34 27 220 as thickeners in cosmetic or pharmaceutical preparations.

EP 452 758 describes hydrocarbon-rich gels for dermal cosmetic and medicinal uses, which, beside various surfactants, contain a water-soluble polymer, such as, for example, polyvinylformamide, as a further constituent.

Body care creams which contain a monoaldehyde-modified vinylamine polymer, are disclosed in U.S. Pat. No. 5,270,379.

Copolymers which are used, for example, as setting lotions and synthesized from N-vinylamide monomers of the formula

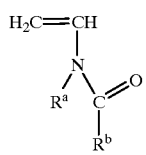

where $R^a$ and $R^b$ are H or $C_1$–$C_5$-alkyl, and the comonomer is selected from among vinyl ethers, vinyllactams, vinyl halides, vinyl esters of monobasic, saturated carboxylic acids, (meth)acrylic acid esters, methacrylamides and methacrylonitriles, and esters, anhydrides and imides of maleic acid, are disclosed in DE 14 95 692.

GB 1,082,016 describes homopolymers of N-vinyl-N-methylacetamide or copolymers of this compound with vinyl esters, vinyl ethers, (meth)acrylic acid esters, methacrylamides and methacrylonitriles, vinyl compounds derived from maleic and fumaric acid, styrene, butadiene and vinyl halides, and their use in shampoo, setting lotion and hairspray formulations.

It is an object of the present invention to make available novel polymers with improved activity in cosmetic preparations.

We have found that this object is achieved according to the invention by the use of water-soluble copolymers, which as characteristic structural elements comprise a) vinylcarboxamide units of the general formula I

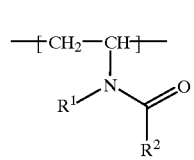

where $R^1$ and $R^2$ independently of one another are H, alkyl, cycloalkyl, aryl or aralkyl, and b) units of the general formula II

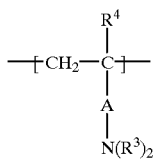

where
A is a chemical bond or an alkylene group,
the radicals $R^3$ independently of one another are H, alkyl, cycloalkyl, aryl or aralkyl, or together with the nitrogen atom to which they are bonded, form an unsubstituted, mono- or polysubstituted, five- to seven-membered, heterocyclic, aromatic or nonaromatic ring, which, if appropriate, contains one or two further heteroatoms, selected from among O, N and S, it being possible for the heterocyclic ring to be fused to a further five- or six-membered, aromatic or nonaromatic ring,
$R^4$ is H, alkyl or aralkyl,
and the corresponding acid addition salts thereof,
as a constituent of cosmetic compositions.

Preferably, the copolymers used according to the invention have a weight-average molecular weight in the range from approximately $10^3$ to $10^8$ g/mol, preferably approximately $10^4$ to $10^7$ g/mol.

If no other details are given, the following definitions apply in the actual description of the invention:

Alkyl radicals which can be used according to the invention comprise straight-chain or branched, saturated hydrocarbon chains having 1 to 12 carbon atoms. Examples which may be mentioned are the following radicals: $C_1-C_6$-alkyl radicals, such as methyl, ethyl, n-propyl, i-propyl, n-butyl, sec-butyl, 2- or 3-methyl-pentyl; and longer-chain radicals, such as unbranched heptyl, octyl, nonyl, decyl, undecyl, lauryl and the single- or multiple-branched analogs thereof.

Alkylene radicals which can be used according to the invention include straight-chain $C_1-C_{10}$-alkylene radicals, such as, for example, methylene, ethylene, propylene, butylene, pentylene and hexylene, and branched $C_1-C_{10}$-alkylene radicals, such as, for example, 1,1-dimethylbutylene, 1,3-dimethylbutylene, 1,2-dimethylpentylene and 1,3-dimethylhexylene. Straight-chain alkylene groups having 1 to 6 carbon atoms, however, are preferred.

Cycloalkyl radicals which can be used according to the invention include, in particular, $C_3-C_{12}$-cycloalkyl radicals, such as, for example, cyclopropyl, cyclobutyl, cyclopentyl, cyclohexyl, cycloheptyl, cyclooctyl, cyclopropylmethyl, cyclopropylethyl, cyclopropylpropyl, cyclobutylmethyl, cyclobutylethyl, cyclopentylethyl, -propyl, -butyl, -pentyl, -hexyl and the like.

Aralkyl radicals suitable according to the invention include phenyl- and naphthyl-$C_1-C_{12}$-alkyl radicals, the $C_1-C_{12}$-alkyl moiety being defined as indicated above. Preferred aralkyl radicals are phenyl-$C_1-C_6$-alkyl radicals.

Suitable aryl radicals according to the invention are, for example, phenyl and naphthyl.

Examples of five- to seven-membered N-heterocyclic radicals which may be mentioned are: five-membered radicals, such as pyrrolyl, pyrrolinyl, pyrrolidinyl; 1,2- and 1,3-oxazolyl, 1,2- and 1,3-thiazolyl; 1,2- and 1,3-oxazolinyl; 1,2- and 1,3-thiazinyl; 1,2- and 1,3-oxazolidinyl; 1,2- and 1,3-thiazolidinyl; pyrazolyl, pyrazolinyl, pyrazolidinyl; imidazolyl, imidazolinyl, imidazolidinyl; 1,2,4-triazolyl, 1,3,4-triazolyl. Six-membered radicals, such as pyridyl and piperidyl; pyridazinyl, pyrimidinyl, pyrazinyl; piperazinyl; 1,2-, 1,3- and 1,4-oxazinyl, morpholinyl, 1,2-, 1,3- and 1,4-thiazinyl; 1,2,3-, 1,2,4- and 1,3,4-triazinyl, 1,2,3-, 1,2,4- and 1,3,4-oxadiazinyl, 1,2,3-, 1,2,4- and 1,3,4-thiadiazinyl. Seven-membered radicals, such as azepinyl, 1,2-, 1,3- and 1,4-diazepinyl, 1,2-, 1,3- and 1,4-oxazepinyl, 1,2-, 1,3- and 1,4-thiazepinyl.

Examples of fused heterocyclic radicals are indolyl, indazolyl, benzimidazolyl, benzoxazolyl, benzothiazolyl; quinolinyl, isoquinolinyl, 1,2-dihydroquinolinyl; phthalazinyl, quinazolinyl, quinoxalinyl; benzodiazepinyl, benzoxazepinyl and benzothiazepinyl.

The heterocyclic radicals according to the invention can be unsubstituted or substituted by one or more, such as, for example, 1, 2 or 3, in particular 1 or 2, substituents. Suitable substituents are selected from among alkyl, cycloalkyl, aryl, aralkyl, OH, O-alkyl, O-aryl, SH, S-alkyl, S-aryl, $NH_2$, NH-alkyl, NH-aryl, $N(alkyl)_2$, if appropriate in protonated form, $N(alkyl)_3^+Z^-$, Z being the radical of an inorganic or organic acid, COOH, CHO, COO-alkyl, $CONH_2$, CONH-alkyl, $CON(alkyl)_2$, CN and $SO_3H$. Alkyl, cycloalkyl, aryl and aralkyl herein have the meanings given above.

As characteristic structural elements, preferred copolymers contain vinylcarboxamide units of the formula I, where $R^1$ and $R^2$ independently of one another are H or alkyl. Particularly preferably, $R^1$ is H and $R^2$ is $C_1-C_6$-alkyl.

As preferred units of the formula II, the copolymers according to the invention contain monomers, where A is a chemical bond or a $C_1-C_6$-alkyl radical, in particular a chemical bond; $R^4$ is H or $C_1-C_6$-alkyl, in particular H; and the radicals $R^3$, together with the nitrogen atom to which they are bonded, are a five- to seven-membered heterocyclic unsubstituted, monosubstituted or polysubstituted ring according to the above definition.

Preferred heterocyclic radicals are five- or six-membered aromatic or nonaromatic rings which may contain a further heteroatom, selected from among O, N and S, preferably N.

If the heterocyclic ring is substituted, it has one or two, preferably one, further substituent. Preferred substituents are $C_1-C_6$-alkyl, —OH, —O—$C_1-C_6$-alkyl, —O-phenyl, —SH, —S—$C_1-C_6$-alkyl, —S-phenyl, —$NH_2$, —NH-$C_1-C_6$-alkyl, —NH-phenyl, —$N(C_1-C_6$-alkyl$)_2$, —$N(C_1-C_6$-alkyl$)_3^+Z^-$, —COOH, —COO—$C_1-C_6$-alkyl, —$CONH_2$, —CONH—$C_1-C_6$-alkyl, —$CON(C_1-C_6$-alkyl$)_2$, —CN and —$SO_3H$.

Preferred counterions $Z^-$ are $Cl^-$, $Br^-$, $H_2PO_4^-$, $SO_4^{2-}$, $NO_3^-$, $HCOO^-$, phenyl-$SO_3^-$. If the heterocycle contains a quaternized nitrogen heteroatom, the counterion $X^-$ has the meanings given for $Z^-$.

Preferred fused heterocycles are benzo-fused heterocyclic rings.

Preferred examples of monomers of the formula I are N-vinylformamide, N-vinyl-N-methylformamide, N-vinyl-N-ethylformamide, N-vinyl-N-propylformamide, N-vinyl-N-isopropylformamide, N-vinyl-N-butylformamide, N-vinyl-N-sec-butylformamide, N-vinyl-N-tert-butylformamide, N-vinyl-N-pentylformamide, N-vinylacetamide, N-vinyl-N-methylacetamide and N-vinyl-N-ethylacetamide.

Preferred examples of monomers of the formula II are unsubstituted, mono- or polysubstituted N-vinylpyrroles, N-vinylimidazoles, N-vinylimidazolines, N-vinylpyridines, N-vinylpyridazines, N-vinylpyrimidines, N-vinylpyrazines, N-vinylindoles, N-vinylindazoles and N-vinylbenzimidazoles.

The heterocyclic functions are present here in the form of the free bases or alternatively neutralized with mineral acids or organic acids or alternatively quaternized, the quaternization preferably being performed using dimethyl sulfate, diethyl sulfate, methyl chloride or benzyl chloride.

Particularly preferred heterocyclic monomers are selected from among imidazole and imidazolium monomers of the following formulae III and IV:

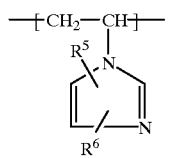
(III)

where
$R^5$ and $R^6$ independently of one another are selected from among H, alkyl, aryl, aralkyl or together are a benzofused ring;

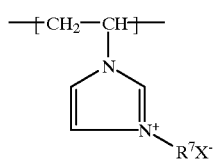
(IV)

where
X is the radical of an inorganic or organic acid and $R^7$ is H, alkyl or aralkyl, and the corresponding imidazoline derivatives.

Particularly preferred monomers of the formula III are compounds where $R^5$ and $R^6$ independently of one another are H or $C_1$–$C_6$-alkyl, in particular H. Particularly preferred monomers of the formula IV are compounds where $R^7$ is $C_1$–$C_6$-alkyl or X is Cl or Br.

Examples of imidazole and imidazoline monomers are N-vinyl-2-methylimidazole, N-vinyl-4-methylimidazole, N-vinyl-5-methylimidazole, N-vinyl-2-ethylimidazole, N-vinyl-N'-methylimidazolium chloride, N-vinyl-N'-ethylimidazolium chloride, N-vinylimidazoline, N-vinyl-2-methylimidazoline and N-vinyl-2-ethylimidazoline.

Preferred copolymers are additionally those comprising
a) from 0.1 to 99.9, preferably from 1 to 99, in particular from 5 to 95, mol % of N-vinylcarboxamide units of the formula I,
b) from 0.1 to 99.9, preferably from 1 to 99, in particular from 5 to 95, molt of units of the formula II,
c) from 0 to 99.8, preferably from 0 to 98, in particular from 0 to 90, mol % of monoethylenically unsaturated monomer units which are different from a) and b); and
d) from 0 to 5, preferably from 0 to 4, in particular from 0 to 3, mol % of monomer units having at least two ethylenically unsaturated double bonds.

Examples of monomers c) are vinylamines and their salts, such as, for example, vinylammonium halides, vinyl alcohol, vinyl formate, vinyl acetate, vinyl propionate, vinyl butyrate, N-vinyl-pyrrolidone, N-vinylcaprolactam, N-vinylureas, $C_1$–$C_6$-vinyl ethers, monoethylenically unsaturated $C_3$–$C_8$-carboxylic acids and -dicarboxylic acids, and their esters, amides, anhydrides and nitriles, olefins and vinylaromatics.

Suitable additional etlylenically unsaturated monomers c) are vinyl formate, vinyl acetate, vinyl propionate, vinyl butyrate, unsaturated $C_3$- to $C_8$-carboxylic acids, such as, for example, acrylic acid, methacrylic acid, maleic acid, crotonic acid, itaconic acid and vinylacetic acid, as well as their alkali metal and alkaline earth metal salts, esters, amides and nitriles, for example methyl acrylate, methyl methacrylate, ethyl acrylate, ethyl methacrylate, propyl acrylate and butyl acrylate or glycol or polyglycol esters of ethylenically unsaturated carboxylic acids, only one OH group each of the glycols and polyglycols being esterified, e.g. hydroxyethyl acrylate, hydroxyethyl methacrylate, hydroxypropyl acrylate, hydroxypropyl methacrylate, hydroxybutyl acrylate, hydroxybutyl methacrylate or alternatively acrylic acid and methacrylic acid monoesters of polyalkylene glycols of a molecular weight from 1500 to 10,000. Also suitable are esters of ethylenically unsaturated carboxylic acids with amino alcohols, such as, for example, dimethylaminoethyl acrylate, dimethylaminoethyl methacrylate, diethylaminoethyl acrylate, diethylaminoethyl methacrylate, dimethylaminopropyl acrylate, dimethylaminopropyl methacrylate, diethylaminopropyl acrylate, diethylaminopropyl methacrylate, dimethylaminobutyl acrylate and diethylaminobutyl acrylate. The basic acrylates are present here in the form of the free bases, the salts with mineral acids, such as, for example, hydrochloric acid, sulfuric acid and nitric acid, the salts of organic acids, such as formic acid or benzenesulfonic acid, or in quaternized form.

Suitable quaternizing agents are, for example, dimethyl sulfate, diethyl sulfate, methyl chloride, ethyl chloride or benzyl chloride.

Suitable monomers c) are additionally unsaturated amides such as, for example, acrylamide, methacrylamide and also N-alkylmono- and -diamides having alkyl radicals from 1 to 6 C-atoms, e.g. N-methylacrylamide, N,N-dimethylacrylamide, N-methylmethyl-acrylamide, N-ethylacrylamide, N-propylacrylamide and tert-butylacrylamide and also basic (meth)acrylamides, such as, for example, dimethylaminoethylacrylamide, dimethylaminoethyl-methacrylamide, diethylaminoethylacrylamide, diethylaminoethyl-methacrylamide, dimethylaminopropylacrylamide, dimethylaminopropylmethacrylamide, diethylaminopropylacrylamide and diethylaminopropylmethacrylamide.

$C_1$–$C_6$-Vinyl ethers, such as, for example, vinyl methyl ether, vinyl ethyl ether, vinyl propyl ether, vinyl isopropyl ether, vinyl butyl ether, vinyl isobutyl ether, vinyl pentyl ether and vinyl hexyl ether can also be employed as monomers c).

Possible monomers c) are furthermore N-vinylpyrrolidone, N-vinyl-caprolactam, N-vinylurea and substituted N-vinylureas, for example N-vinyl-N'-methylurea and N-vinyl-N'-dimethylurea.

Monomers c) which can also be employed are monoethylenically unsaturated compounds having sulfo groups, such as, for example, vinylsulfonic acid, allylsulfonic acid, methallylsulfonic acid, styrenesulfonic acid or 3-sulfopropyl acrylate, 3-sulfopropyl methacrylate and 2-acrylamido-2-methylpropanesulfonic acid. The compounds having acid groups can be present in the form of the free acids, and the ammonium, alkali metal and alkaline earth metal salts.

A further modification of the copolymers can be achieved by additionally copolymerizing 0 to 5 mol % units of monomers d) with at least two ethylenically unsaturated nonconjugated double bonds. Comonomers of this type are customarily used in copolymerizations as crosslinkers. The additional use of these comonomers during the copolymerization causes an increase in the molar masses of the copolymers. Suitable compounds of this type are, for example, methylenebisacrylamide, esters of acrylic acid and methacrylic acid with polyhydric alcohols, e.g. glycol diacrylate, glycerol triacrylate, glycol dimethacrylate, glycerol trimethacrylate and also polyols esterified at least twice with acrylic acid or methacrylic acid, such as pentaerythritol and glucose. Suitable crosslinkers are additionally divinylbenzene, divinyldioxane, pentaerythritol triallyl ether, pentaallyl-sucrose, divinylurea and divinylethyleneurea.

The copolymers to be employed according to the invention are obtained according to the process known from the literature of free radical-initiated copolymerization of monomers of the formula I (monomers a)) and of the formula II (monomers b)) and, if appropriate, in the presence of the abovementioned further monomers c) and/or d) and possibly subsequent partial removal of the carbonyl group by hydrolysis. Suitable preparation processes are described, for example, in EP-A-0 071 050, EP-A-0 251 182 and EP-A-0 216 387, to which reference is hereby expressly made.

The polymerization can be carried out in the presence or alternatively in the absence of an inert solvent or diluent. Since the polymerization in the absence of inert solvents or diluents usually leads to inhomogeneous polymerizates, polymerization in an inert solvent or diluent is preferred. Suitable inert solvents, for example, are those in which the open-chain N-vinylcarboxamides are soluble. Suitable solvents for solution polymerization are, for example, inert solvents, such as methanol, ethanol, isopropanol, n-propanol, n-butanol, tetrahydrofuran, dioxane, water and mixtures of the inert solvents mentioned. The polymerization can be carried out continuously or batchwise. It is carried out in the presence of free radical-forming initiators, which are employed in amounts from 0.01 to 20, preferably 0.05 to 10,% by weight, based on the monomers. If appropriate, the polymerization can also be initiated solely by the action of energy-rich radiation, e.g. electron beams or UV rays.

In order to prepare polymers having low molecular weights, e.g. from 1000 to 100,000, preferably from 5000 to 50,000, the polymerization is expediently carried out in the presence of regulators. Suitable regulators are, for example, organic compounds which contain sulfur in bound form. These include mercapto compounds, such as mercaptoethanol, mercaptopropanol, mercaptobutanol, mercaptoacetic acid, mercaptopropionic acid, butyl mercaptan and dodecyl mercaptan. Suitable regulators are additionally allyl compounds, such as allyl alcohol, aldehydes, such as formaldehyde, acetaldehyde, propionaldehyde, n-butyraldehyde and isobutyraldehyde, formic acid, ammonium formate, propionic acid, hydrazine sulfate and butenols.

If the polymerization is carried out in the presence of regulators, 0.05 to 20% by weight thereof is needed, based on the monomers employed in the polymerization.

The polymerization of the monomers is customarily carried out in an inert gas atmosphere with exclusion of atmospheric oxygen. During the polymerization, provision is in general made for thorough mixing of the reaction participants. With relatively small batches, in which safe dissipation of the heat of polymerization is guaranteed, the monomers can be polymerized batchwise by heating the reaction mixture to the polymerization temperature and then allowing the reaction to proceed. These temperatures are in this case in the range from 40 to 180° C., it being possible to work under normal pressure, reduced pressure or alternatively elevated pressure. Polymers having a high molecular weight are obtained when the polymerization is carried out in water. For the preparation of water-soluble polymers, for example, this can be carried out in aqueous solution, as a water-in-oil emulsion or according to the reverse suspension polymerization process.

In order to avoid hydrolysis of the monomeric N-vinylcarboxamides during the polymerization in aqueous solution, the polymerization is preferably carried out in a pH range from 4 to 9, in particular from 5 to 8. In many cases, it is recommended additionally to work in the presence of buffers, e.g. primary or secondary sodium phosphate.

From the polymers described above, if appropriate by partial removal of the group

from the N-vinylcarboxamide units with formation of amine or ammonium groups, copolymers which can be used according to the invention are obtained which, as monomer c), contain a vinylamine or its corresponding ammonium compound. The hydrolysis is preferably carried out in water under the action of acids, bases or enzymes, but can also be carried out in the absence of the hydrolyzing agents mentioned. Depending on the reaction conditions in the hydrolysis, i.e. the amount of acid or base, based on the polymer to be hydrolyzed, and also reaction time and temperature, various degrees of hydrolysis are obtained. The hydrolysis is carried out until from 0.1 to 99.9 mol %, preferably from 1 to 99 mol % and very particularly preferably from 5 to 95 mol %, of the carboxamide radicals are hydrolytically cleaved.

Acids suitable for the hydrolysis are, for example, mineral acids, such as hydrogen halide (gaseous or in aqueous solution), sulfuric acid, nitric acid, phosphoric acid (ortho-, meta- or polyphosphoric acid) or organic acids, e.g. $C_1$- to $C_5$-carboxylic acids such as formic acid, acetic acid or propionic acid or aliphatic and aromatic sulfonic acids, such as methanesulfonic acid, benzenesulfonic acid or toluenesulfonic acid. In the case of hydrolysis with acids, the pH is from 0 to 5. Per carboxylic acid radical to be removed in the polymer, from 0.05 to 1.5 equivalents of acid are needed, preferably from 0.4 to 1.2.

In the case of hydrolysis with bases, metal hydroxides of metals of the first and second main group of the Periodic Table can be used, for example lithium hydroxide, sodium hydroxide, potassium hydroxide, calcium hydroxide, strontium hydroxide and barium hydroxide. However, ammonia or alkyl derivatives of ammonia are also suitable, e.g. alkyl- or arylamines, such as triethylamine, monoethanolamine, diethanolamine, triethanolamine, morpholine, piperidine, pyrrolidine or aniline. In the case of hydrolysis with bases, the pH is from 8 to 14. The bases can be employed diluted or undiluted in the solid, liquid or, if appropriate, also the gaseous state. Ammonia, sodium hydroxide solution or potassium hydroxide solution is preferably used. Hydrolysis in the acidic or alkaline pH range is carried out at from 20 to 170° C., preferably from 50 to 120° C. It is complete after from approximately 2 to 8, preferably from 3 to 5, hours.

A procedure has proven particularly suitable in which the acids or bases are added in aqueous solution. After the hydrolysis, inter alia, a neutralization is carried out such that the pH of the hydrolyzed polymer solution is from 2 to 8, preferably from 3 to 7. Neutralization is necessary if it is intended to avoid or delay progress of the hydrolysis of partially hydrolyzed polymers. The hydrolysis can also be carried out with the aid of enzymes.

In the case of the hydrolysis of copolymers containing N-vinylcarboxamide units, if appropriate a further modification of the polymers is carried out to the effect that the copolymerized comonomers are also hydrolyzed. Vinyl alcohol units are thus formed, for example, from copolymerized units of vinyl esters. Depending on the hydrolysis conditions, the copolymerized vinyl esters can be completely or partially hydrolyzed.

In the case of partial hydrolysis of copolymers containing vinyl acetate units, the hydrolyzed copolymer comprises, beside unchanged vinyl acetate units, vinyl alcohol units as well as N-vinylcarboxamide and vinylamine units. Carboxylic acid units are formed in the hydrolysis from units of monoethylenically unsaturated carboxylic acid anhydrides, esters and amides.

Copolymerized, monoethylenically unsaturated carboxylic acids themselves are unchanged in the hydrolysis. Carboxamide and carboxylic acid units can also be formed from copolymerized, monoethylenically unsaturated nitriles. The degree of hydrolysis of the copolymerized comonomers can easily be determined analytically.

The amine functions can be present either in the form of the free bases or, neutralized with mineral acids or organic acids, such as, for example, formic acid, acetic acid, valeric acid, 2-ethylhexanoic acid, lauric acid, adipic acid, benzoic acid, p-methoxybenzoic acid, lactic acid, citric acid, in salt form. The possibility further exists of alkylating or of quaternizing unsubstituted amine groups. Alkylation and quaternization is in this case carried out with the aid of customary alkylating agents, such as alkyl halides, e.g. methyl chloride, methyl bromide, methyl iodide, ethyl bromide, ethyl iodide or benzyl bromide, or alternatively dimethyl sulfate or diethyl sulfate. The reaction can in this case be carried out in aqueous medium, in inert organic solvents or alternatively in mixtures of water with solvents, if appropriate with phase-transfer catalysis. Preferably, the alkylation and quaternization are carried out in aqueous medium.

The copolymers used according to the invention have molecular weights of from 1000 to 10 million, preferably from 10,000 to 5 million, which corresponds to K values from approximately 5 to 300 or 10 to 250, measured on 1% strength aqueous solutions at pH 7 and 25° C. according to H. Fikentscher, Cellulose-Chemie [Cellulose Chemistry], Volume 13, 58 to 64 and 71 to 74 (1932).

The copolymers described above are used as active ingredients in cosmetic preparations, for example as conditioners for shampoos, hair treatments, lotions, emulsions, rinses, gels, foams and pre- and aftertreatment agents for hair dyeing and permanent waving and as setting lotions and hair styling agents having caring properties. They can furthermore be used as thickeners in cosmetic formulations and in cosmetic preparations for oral hygiene.

It has surprisingly been found that the N-vinylformamide copolymers according to the invention have improved properties in cosmetic formulations. These improvements in properties are most striking in shampoo formulations. The copolymers according to the invention are preferably used in customary market shampoo formulations having sodium or ammonium lauryl ether sulfate as a base surfactant and, if appropriate, further cosurfactants, e.g. alkyl polyglycosides, cocamidopropylbetaines, sulfosuccinic acid esters, sec-alkanesulfonates, α-olefinsulfonates, protein-fatty acid condensates, N-acylsarcosinates, taurides, methyltaurides, fatty acid isethionates, N-acylglutamates, ethercarboxylic acid derivatives, alkylphosphate esters, alkylbetaines, alkylamidopropylbetaines, sulfobetaines, alkylglyceryl ethersulfonates, coconutamphocarboxyglycinates and sorbitan derivatives. After use of the N-vinylformamide copolymers in the abovementioned shampoos, the wet combability of the hair, in particular, is improved. Moreover, luster, volume and body as well as outstanding strength are imparted to the hair. The shampoos thus have washing, conditioning and setting action (3 in 1 shampoos), the polymers being effective even in low use amounts.

The copolymers according to the invention also show good conditioning and setting effects in hair treatments, lotions, emulsions, rinses and styling agents, such as gels and foams, and in pre- and after treatment agents for hair dyeing and permanent waving, where they result in excellent caring properties.

Furthermore, the copolymers can also be employed as conditioning agents and thickeners in skin care compositions, such as creams, ointments, emulsions and lotions, as well as for oral hygiene in toothpastes, gels and mouthwashes.

The invention thus also relates to cosmetic compositions comprising at least one polymer according to the above definition in a cosmetic carrier and, if appropriate, in combination with further cosmetically active substances.

The polymers according to the invention are usually contained in the cosmetic compositions in an amount from approximately 0.01 to 15% by weight, such as, for example, from approximately 0.1 to 10% by weight, based on the total weight of the composition. Beside customary cosmetic carriers, further customary additives, such as, for example, surface-active agents, thickening agents, gel-forming agents, solubilizers, moisture-retaining agents, binders, propellants, polymers, such as, for example, silicones, sequestering agents, chelating agents, viscosity modifiers, opacifying agents, stabilizers, pearl luster agents, colorants, fragrances, organic solvents, preservatives, pH-adjusting agents and, if appropriate, further conditioning agents can be contained.

The invention will now be illustrated in greater detail by means of the following, nonlimiting examples.

PREPARATION EXAMPLE

Preparation of copolymer of 90 mol % of N-vinylformamide and 10 mol % of N-vinyl-N'-methylimidazolium chloride (Copolymer 1).

A mixture of 180 g of N-vinylformamide, 44.4 g of a 45% strength aqueous solution of N-vinyl-N'-methylimidazolium chloride and 775.6 g of water was heated to 70° C. under nitrogen in a laboratory apparatus having a reflux condenser and anchor stirrer. After addition of a solution of 0.6 g of 2,2'-azobis(2-amidinopropane) dihydrochloride in 10 ml of water, the temperature of 70° C. was maintained for 8 hours with stirring. In the course of this, a fall in the pH below a value of 7 was prevented by addition of ammonia during the polymerization. After cooling the reaction mixture, a clear, colorless polymer solution having a solids content of 20.1% was obtained. The K value of the polymer (measured at 0.1% strength in 5% strength sodium chloride solution) was 104. The determination of the K value is described in H. Fikentscher "Systematik der Cellulosen auf Grund ihrer Viskosität in Lösung" [Systematology of celluloses on the basis of their viscosity in solution], Cellulose-Chemie 13, (1932) 58–64 and 71–74.

USE EXAMPLE

Copolymer 1 according to the preparation example was compared with the known copolymers 2 and 3 with respect to its hair conditioning action.

Copolymer 2 (Prior art)

Commercially available copolymer of acrylamide and diallyldimethylammonium chloride having a molecular weight of about 1,000,000 (Merquat S from Merck Calgon).

Copolymer 3 (Prior art)

Commercially available cationic hydroxyethylcellulose (Celquat H 100 from National Starch & Chem. Inv. Hold. Corp.).

For testing as conditioning agents for hair shampoos, the copolymers 1 to 3 mentioned were added in the amounts indicated to a standard test shampoo containing 15.0% by weight of sodium lauryl ether sulfate having 2 to 3 ethylene oxide units (Texapon NSO from Henkel KG). By means of defined hair tresses, the effect of the polymers on the wet combability was tested. To do this, the hair tresses were washed with the polymer-containing test shampoo and rinsed and the combing force was then measured. A hair tress which had been treated with test shampoo without addition was used as a blank sample. The results are shown in Table 1.

TABLE 1

| Copolymer | Amount added [% as such] | Combing force decrease [with respect to blank value] |
|---|---|---|
| 1 | 0.1 | 43 |
| 2 | 0.1 | 5 |
|   | 1.0 | 18 |
| 3 | 0.1 | 25 |

The combing force decrease is calculated according to the following formula:

$$\text{Decrease }[\%] = \left[\frac{\text{measured value} \times 100}{\text{Blank value}}\right] - 100$$

Accordingly, high combing force decreases are to be assessed as positive.

We claim:

1. A cosmetic composition containing at least one water-soluble copolymer which comprises as characteristic structural elements a) vinylcarboxamide units of the formula I

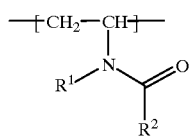

(I)

where $R^1$ and $R^2$ independently of one another are H, alkyl, cycloalkyl, aryl or aralkyl, and b) heterocyclic units selected from the grout consisting of i)

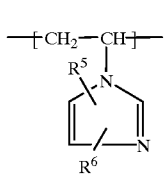

(III)

where $R^5$ and $R^6$ independently of one another are H, alkyl, aryl or aralkyl or together are a benzo-fused ring; and ii)

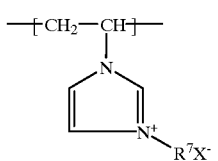

(IV)

where

X is the radical of an inorganic or organic add and $R^7$ is H, alkyl or aralkyl; in a cosmetic carrier and, optionally in combination with further cosmetically active substances.

2. The composition as claimed in claim 1, wherein the copolymer has a weight-average molecular weight in the range from $10^3$ to $10^8$ g/mol.

3. The composition as claimed in claim 1, wherein said water-soluble copolymer comprises a) from 0.1 to 99.9% mol % of N-vinylcarboxamide units of the formula I, b) from 0.1 to 99.9 mol % of heterocyclic units of the formula III and/or IV, c) from 0 to 99.8 mol % of monoethylenically unsaturated monomer units which are different from a) and b); and d) from 0 to 5 mol % of monomer units having at least two ethylenically unsaturated double bonds.

4. The composition as claimed in claim 3, wherein the monomer units c) are derived from vinyl alcohol; vinyl formate, vinyl acetate, vinyl propionate; vinyl butyrate; N-vinylpyrrolidone; N-vinyl caprolactam; N-vinyl ureas; $C_1$–$C_6$-vinyl ethers; monoethylenically unsaturated $C_3$–$C_8$-carboxylic acids or -dicarboxylic acids or their esters, amides, anhydrides or nitrites; olefins, vinylaromatics, vinylimines, vinylammonium halides or monomers containing sulfonic acid groups having a polymerizable double bond.

5. The composition of a copolymer as claimed in claim 1, containing said copolymer as a conditioner or thickening agent.

6. The composition as claimed in claim 1, which are hair cosmetic compositions, skin care compositions or oral hygiene compositions.

7. The composition as claimed in claim 6, selected from the class consisting of setting lotions, hair treatments, lotions, emulsions, rinses, gels, foams, pre- and aftertreatment agents for hair dyeing and permanent waving, hair-styling agents and shampoos.

8. The composition as claimed in claim 7, in the form of a shampoo containing said copolymer as conditioner.

9. The composition as claimed in claim 1, containing the water-soluble copolymers in an amount from 0.01 to 15% by weight, based on the total weight of the composition.

10. The composition as claimed in claim 1, containing at least one additive, selected from the group consisting of surface-active agents, thickening agents, gel-forming agents, solubilizers, moisture-retaining agents, binders, propellants, polymers, sequestering agents, chelating agents, viscosity modifiers, opacifying agents, stabilizers, pearl luster agents, colorants, fragrances, preservatives and pH-adjusting agents.

11. A method for the treatment of hair or skin, which comprises applying a cosmetic composition as claimed in claim 1 to said hair or skin.

* * * * *

UNITED STATES PATENT AND TRADEMARK OFFICE
CERTIFICATE OF CORRECTION

| | |
|---|---|
| PATENT NO. : 6,231,876 B1 | Page 1 of 1 |
| DATED : May 15, 2001 | |
| INVENTOR(S) : Niessner et al. | |

It is certified that error appears in the above-identified patent and that said Letters Patent is hereby corrected as shown below:

<u>Column 12, claim 1,</u>
Line 29, "organic add" should be -- organic acid --.

Signed and Sealed this

Thirtieth Day of October, 2001

Attest:

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO. : 6,231,876 B1
DATED : May 15, 2001
INVENTOR(S) : Niessner et al.

It is certified that error appears in the above-identified patent and that said Letters Patent is hereby corrected as shown below:

Column 1,
Line 47, "vinylpyrolidone" should be -- Vinylpyrolidone --.

Column 6,
Line 5, "nitrites" should be -- nitriles --.
Line 21, "dimethylamionbutyl" should be -- dimethylaminobutyl --.

Column 9,
Line 19, "nitrides" should be -- nitriles --.

Column 12,
Line 53, "nitrites" should be -- nitriles --.

Signed and Sealed this

Seventh Day of January, 2003

JAMES E. ROGAN
*Director of the United States Patent and Trademark Office*